United States Patent
Avendano et al.

(10) Patent No.: US 6,525,063 B2
(45) Date of Patent: Feb. 25, 2003

(54) ANTITUMOUR 1,5-DIAZAANTHRAQUINONES

(75) Inventors: Carmen Avendano, Madrid (ES); José María Perez, Madrid (ES); Maria del Mar Blanco, Madrid (ES); José Carlos Menendez, Madrid (ES); Dolores Garcia Gravalos, Tres Cantos (ES); Jesús Angel de la Fuente, Onzonilla (ES); María Jesús Martin, Onzonilla (ES)

(73) Assignee: Universidad Complutense de Madrid, Madrid (ES)

( * ) Notice: Subject to any disclaimer, the term of this patent is extended or adjusted under 35 U.S.C. 154(b) by 0 days.

(21) Appl. No.: 09/903,407

(22) Filed: Jul. 11, 2001

(65) Prior Publication Data

US 2002/0099066 A1 Jul. 25, 2002

Related U.S. Application Data

(63) Continuation of application No. 09/700,941, filed as application No. PCT/GB99/01619 on May 21, 1999, now abandoned.

(30) Foreign Application Priority Data

May 21, 1998 (GB) ............................................. 9810998

(51) Int. Cl.[7] .................. A61K 31/4745; C07D 471/04; A61P 35/00
(52) U.S. Cl. ......................... 514/292; 514/290; 546/81; 546/79
(58) Field of Search ..................... 546/81, 79; 514/292, 514/290

(56) References Cited

FOREIGN PATENT DOCUMENTS

| EP | 0 574 195 A1 | 12/1993 |
| EP | 0 695 752 A1 | 7/1996 |

OTHER PUBLICATIONS

Sofina et al. Experimental Evaluation of Antiumor Drugs in the USA and USSR and Clinical Correlations. NIH Publication No. 80–1933. (1980). pp. 76–78.*

Kitahara et al., "Synthesis of Cystodamine, a Pentacyclic Aza–aromatic Alkaloid", *Tetrahedron Letters*, vol. 38, No. 25, pp. 4441–4442. (1997).

Tapia et al., "Approach to the Synthesis of 1,5–Diazaanthraquinones by Diels–Alder Reactions of Quinoline–5,8–Diones", *Heterocycles*, vol. 43, No. 2, 1995, pp. 447–461.

Gesto et al., "Synthesis of Diaza–Anthraquinones by Hetero Diels–Alder Cycloaddition Reactions", *Tetrahedron Letters*, vol. 45, No. 14, pp. 44774484 (1989).

Krapcho et al., *Current Medicinal Chemistry* (1995), vol. 2, pp. 803–824.

* cited by examiner

*Primary Examiner*—Evelyn Mei Huang
(74) *Attorney, Agent, or Firm*—Ernest V. Linek; Banner & Witcoff, Ltd.

(57) ABSTRACT

Compounds having formula (I) wherein $R^3$, $R^4$, $R^7$ and $R^8$ are independently selected from the group consisting of hydrogen, lower alkyl, halogen, amine, mono(lower)alkylamine, di(lower)alkylamine, phenyl, or substituted phenyl possess antitumor activity and are new with the exception of the compound in which $R^3$, $R^4$, $R^7$, $R^8$ are all hydrogen and the compound in which $R^3$ and $R^7$ are hydrogen, $R^4$ is chlorine, and $R^8$ is a 2-nitrophenyl group.

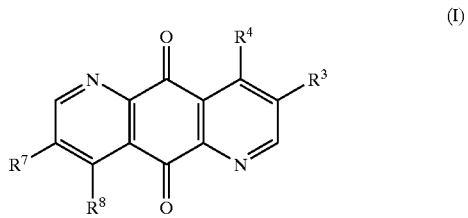

(I)

9 Claims, No Drawings

ANTITUMOUR 1,5-DIAZAANTHRAQUINONES

CROSS-REFERENCE TO RELATED APPLICATIONS

This application is a continuation of commonly owned U.S. patent application Ser. No. 09/700,941, filed Nov. 21, 2000, now abandoned, which application claimed priority under 35 U.S.C. §371 of commonly owned PCT Application No. PCT/GB99/01613, filed May 21, 1999, which application claimed priority of commonly owned British Patent Application No. 9810998.6, filed May 21, 1998. The PCT application designated the United States and was published in the English language on Nov. 25, 1999 as WO 99/599962.

The present invention relates to antitumour 1,5-diazaanthraquinones.

BACKGROUND OF THE INVENTION

Natural products containing a 9,10-anthracenedione substructure are an important class of antitumour compounds. They include anthracyclines (see a) Lown, J. W. Chem. Soc. Rev. 1993, 22, 165; and b) Sengupta, S. K., in Foye, W. O. (ed.). Cancer Chemotherapeutic Agents, Chapter 5. American Chemical Society, 1995), the pluramycins (see (a) Abe, N.; Enoki, N.; Nakakita, Y.; Uchida, H.; Nakamura, T.; Munekata, M. J. Antibiot. 1993, 46, 1536 and references therein; and b) Hansen, M.; Hurley, L. J. Am. Chem. Soc. 1995, 117, 2421) and some of the enediyne antibiotics (see a) Konishi, M.; Ohkuma, H.; Tsuno, T.; Oki, T.; Van Duyne, G. D.; Clardy, J. J. Am. Chem. Soc. 1990, 112, 3715; and b) Nicolau, K. C.; Dai, W.-M.; Hong, Y. P.; Tsay, S.-C.; Baldridge, K. K.; Siegel, J. S. J. Am. Chem. Soc. 1993, 115, 7944). At least in the case of the anthracyclines, the antitumour activity of these quinones is attributed to formation of DNA damaging anion-radical intermediates by reduction of the quinone unit (see a) Pan, S.-S; Pedersen, L.; Bachur, N. R; Mol. Pharmacol. 1981, 19, 184; and b) Hertzberg, R. P.; Dervan, P. B. Biochemistry 1984, 23, 3934).

Isosteric substitution of one or more carbons of the benzene rings by nitrogen atoms should afford compounds with geometries similar to those of the parent compounds, but with increased affinity for DNA due to the presence of sites suitable for hydrogen bonding or ionic interactions. Also, the electron-withdrawing properties of the heterocyclic rings would facilitate the formation of anion-radicals. For these reasons, the preparation of azaanthraquinones as potential antitumour agents is an active field of research (see Krapcho, A. P.; Maresch, M. J.; Hacker, M. P.; Hazelhurst, L.; Menta, E.; Oliva, A; Spinelli, S.; Beggiolin, G.; Giuliani, F. C.; Pezzoni, G.; Tignella, S. Curr. Med Chem. 1995, 2, 803).

Although the considerations outlined above would apply particularly well to diazaanthraquinones, these compounds have receive little attention (see a) Tapia, R. A., Quintanar, C.; Valderrama, J. A., Heterocycles, 1996, 43, 447; and Brassard, P.; Lévesque, S, Heterocycles, 1994, 38, 2205).

SUMMARY OF THE INVENTION

This invention describes a new family of antitumour compounds having the formula (I):

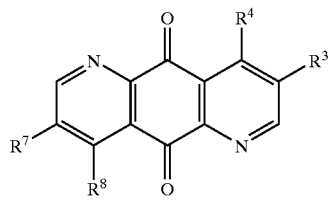

wherein $R^3$, $R^4$, $R^7$, and $R^8$ are independently selected from the group consisting of hydrogen, lower alkyl, halogen, amine, mono(lower)alkylamine, phenyl, or substituted phenyl. The compounds are new, with the exception of the compound in which $R^3$, $R^4$, $R^7$, $R^8$ are all hydrogen, the compound in which $R^3$ and $R^7$ are hydrogen, $R^4$ is chlorine, and $R^8$ is a 2-nitrophenyl group, the compound in which $R^3$ and $R^7$ are hydrogen, $R^4$ is amino, and $R^8$ is a 2-nitrophenyl group, the comound in which $R^3$, $R^7$ and $R^8$ are hydrogen and $R^4$ is chlorine, and the compound in which $R^4$, $R^7$ and $R^8$ are hydrogen and $R^3$ is methyl.

The present invention also provides a method of treating a mammal affected by a malignant tumour sensitive to a compound with the formula (I), which comprises administering a therapeutically effective amount of a compound with the formula (I), or a pharmaceutical composition thereof.

The present invention further provides pharmaceutical compositions which contain a pharmaceutically acceptable carrier and as active ingredient a compound with the formula (I), as well as a process for its preparation.

The compounds can be made by preparative methods in accordance with this invention.

Preferred Embodiments

In the definitions of the groups $R^3$, $R^4$, $R^7$, and $R^8$ in formula (I), the lower alkyl is a straight-chain or branched alkyl group having 1 to 6 carbon atoms, such as methyl, ethyl, propyl, isopropyl, butyl, isobutyl, sec-butyl, tert-butyl, pentyl, neopentyl or hexyl. The substituted phenyl group is preferably substituted with 1 to 4, more preferably 1 or 2 substituents, chosen from lower alkyl, halogen, amine, mono (lower)alkylamine, di(lower)alkylamine, nitro, hydroxy, lower alkoxy, or trifluoromethyl.

Preferred classes of compounds include those of formulae (4), (8), (11), (13), and (14). In these compounds, the substituent groups $R^3$, $R^4$, $R^7$, and $R^8$ are preferably chosen as appropriate from hydrogen, methyl, ethyl, chlorine, dimethylamine, and nitrophenyl.

Examples of pharmaceutical compositions include any solid (tablets, pills, capsules, granules, etc.) or liquid (solutions, suspensions or emulsions) with suitable formulation of oral, topical or parenteral administration, and they may contain the pure compound or in combination with any carrier or other pharmacologically active compounds. These compositions may need to be sterile when administered parenterally.

The correct dosage of a pharmaceutical composition comprising compounds with the formula (I), will vary according to the pharmaceutical formulation, the mode of application, and the particular situs, host and tumour being treated. Other factors like age, body weight, sex, diet, time of administration, rate of excretion, condition of the host drug combinations, reaction sensitivities and severity of the disease shall be taken into account. Administration can be carried out continuously or periodically within the maximum tolerated dose.

In accordance with the preparative methods of this invention, we describe the preparation of five different series of derivatives of the 1,5-diazaanthracene-9,10-dione system, having the formula (I).

Symmetrically substituted derivatives of the 1,5-diazaanthraquinone system (Scheme 1, compounds 4) were prepared by a double hetero Diels-Alder strategy. Thus, 2,5-dibromobenzoquinone (2) was prepared by oxidation of the corresponding hydroquinone (1) with cerium ammonium nitrate (CAN), and treated with 1-dimethylamino-1-azadienes (3) (see Pérez, J. M.; Avendaño, C.; Menéndez, J. C., *Tetrahedron Lett.*, 1997, 38, 4717) to give compounds (4):

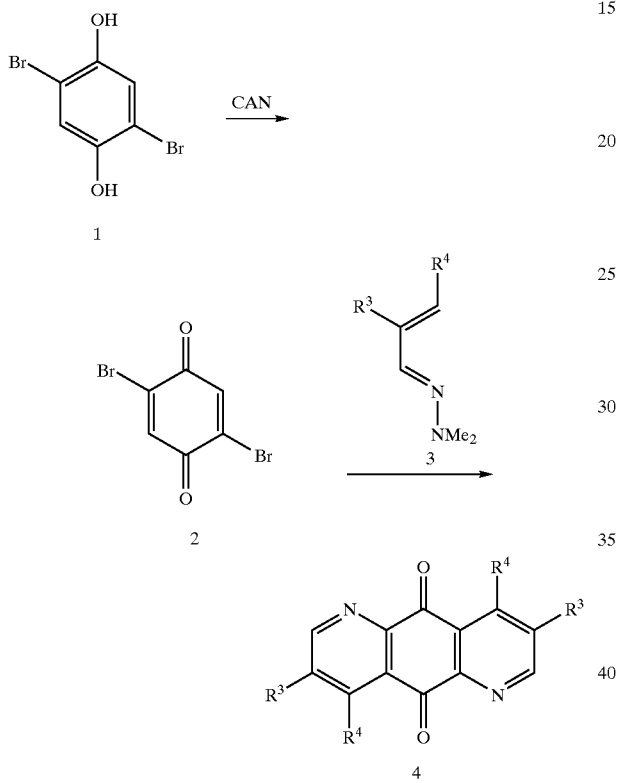

As examples of symmetrically substituted derivatives we have prepared: (4a), (4b), (4c), and (4d):

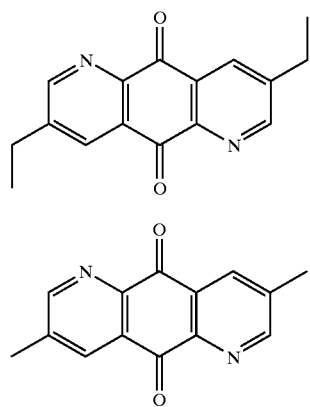

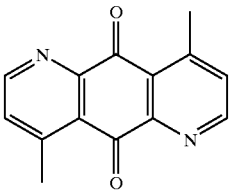

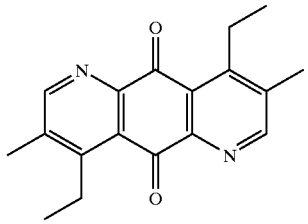

Unsymmetrically substituted derivatives of the 1,5-diazaanthraquinone system were prepared as shown in Scheme 2. Oxidative demethylation of compounds (5) with cerium ammonium nitrate (CAN) afforded quinones (6), whose treatment with the corresponding 1-dimethylamino-1-azadienes (7) gave the derivatives (8).

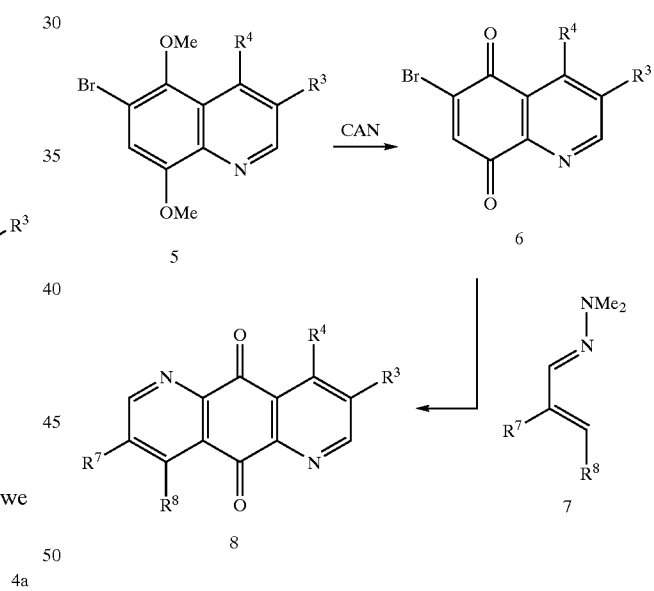

More particularly, as examples of unsymmetrically substituted derivatives, oxidative demethylation of compound (9) (see Waldner, A. *Helv. Chim. Acta,* 1988, 71, 486) with cerium ammonium nitrate (CAN) afforded quinone (10), whose treatment with 3-substituted 1-dimethylamino-1-azadienes gave directly the aromatized derivatives (11). On the other hand, use of 4-substituted 1-dimethylamino-1-azadienes led to compounds (12), which were aromatized by elimination of dimethylamine under thermal conditions to give compounds (13). Treatment of compounds (12) with dilute HCl led to aromatization with concomitant reaction of dimethylamine with the C-8 position, affording compounds (14):

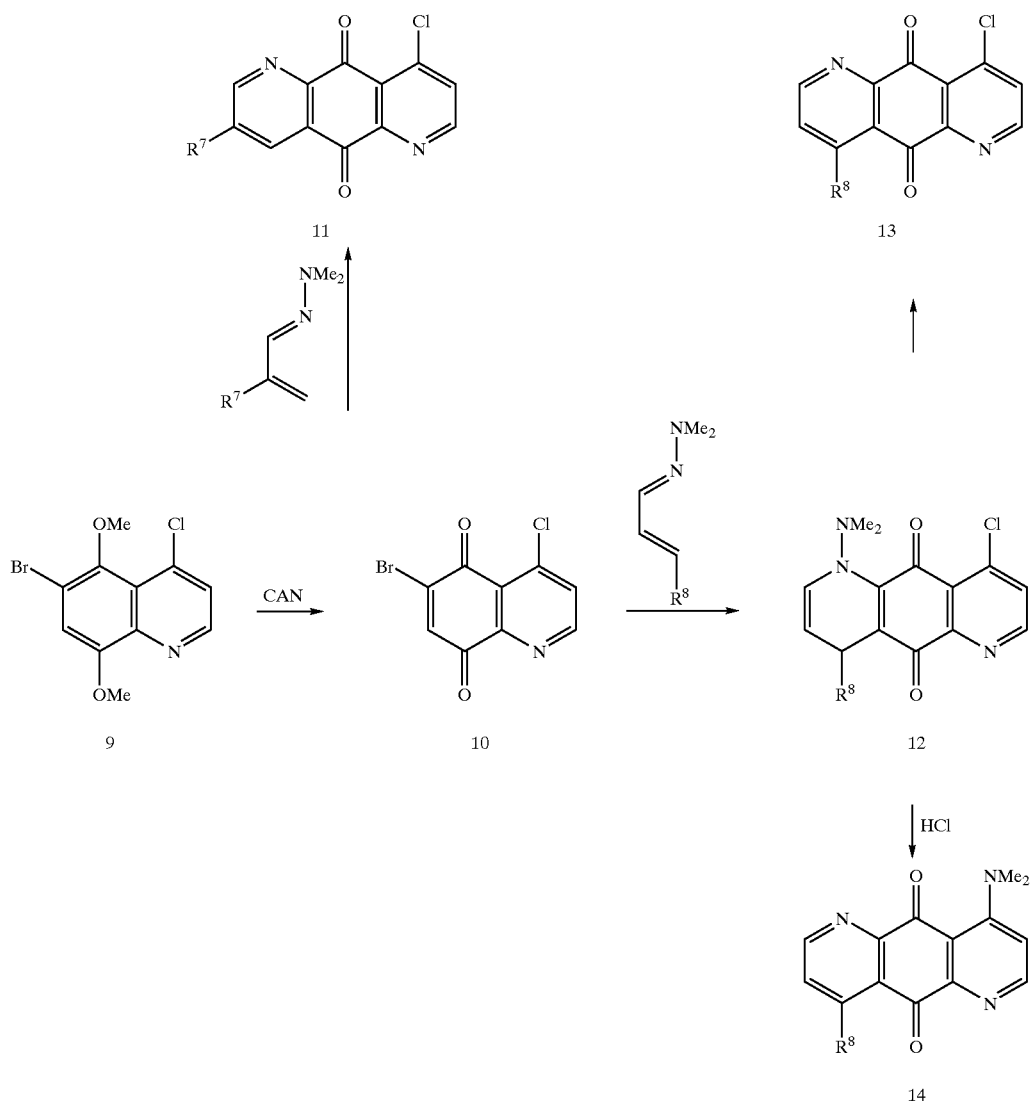
As examples of unsymmetrically substituted derivatives we have prepared: (11a), (12a), (13a), (13b), and (14a):
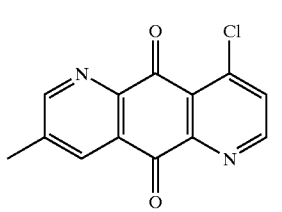
11a
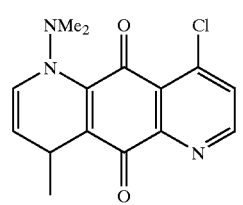
12a
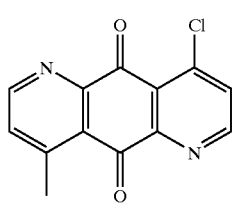
13a
-continued
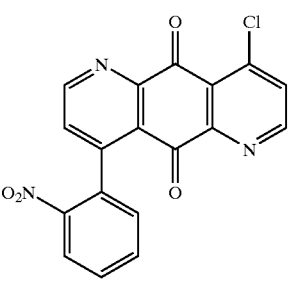
13b

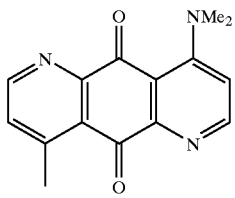

14a (13b) was previously described (see Gómez-Bengoa, E.; Echavarren, A. M., *J Org. Chem.*, 1991, 56, 3497) by us as an intermediate in the synthesis of pyrido(2,3,4-kl)acridines.

(4a), (4b), (4c), (4d), (11a), (12a), (13a), (13b), and (14a) exhibit antitumour activity. In particular, they exhibits antitumour activity against cell lines derived from human solid tumours, such as human lung carcinoma, human colon carcinoma and human melanoma, and, the like, it is active against other tumour cell lines, like leukemia and lymphoma.

A preferred further aspect of the invention is a method for preparing the compounds (4a), (4b), (4c), (4d), (11a), (12a), (13a), and (14a).

EXPERIMENTAL

The reagents used were of commercial origin (Aldrich, Fluka) and were employed without further purification. Solvents (SDS, Schariau) were purified and dried by standard procedures. Reactions were monitored by thin-layer chromatography, using Macherey-Nagel plates with fluorescent indicator. Separations by flash liquid chromatography were performed using silica gel SDS 60 ACC (230–400 mesh).

Melting points are uncorrected, and were determined in open capillary tubes, using a Büchi immersion apparatus or a Hoffler hot stage microscope. Spectroscopic data were obtained with the following instruments: IR, Perkin Elmer Paragon 1000 FT-IR; NMR, Varian VXR-300 (300 MHz for $^1$H and 75 MHz for $^{13}$C) or Bruker AC-250 (250 MHz for $^1$H and 63 MHz for $^{13}$C). Combustion elemental analyses were obtained by the Servicio de Microanálisis Elemental, Universidad Complutense, using a Perkin Elmer 2400 CHN analyzer.

The detailed preparation of some examples of the title compounds is given below.

Symmetrically Substituted 1,5-Diazaanthraquinones. General Procedure.
a) 2,5-Dibromobenzoquinone (2)

To a solution of 2,5-dibromohydroquinone (1) (5 g, 18.6 mol) in acetonitrile (250 ml) was added cerium ammonium nitrate (21.4 g, 39.0 mmol), in small portions. The clear orange solution was stirred for 10 min at room temperature, diluted with water (80 ml) and extracted with chloroform (3×200 ml). The combined chloroform layers were dried over sodium sulphate and evaporated, yielding 3.5 g (71%) of the quinone (2).

IR (KBr): 1657.0 (C=O) cm$^{-1}$.
$^1$H-NMR (300 MHz, CDCl$_3$) δ: 7.48 (s, 2H, H-3,6) ppm.
$^{13}$C-NMR (75 MHz, CDCl$_3$) δ: 176.97 (C-1,4); 137.79 (C-3,6); 137.04 (C-2,5) ppm.

b) Double hetero Diels-Alder reactions

To a solution of 2,5-dibromobenzoquinone (2) (100–200 mg, 0.375–0.750 mmol) in chloroform (10–15 ml) was added the suitable azadiene (3) (2 eq.), and in the case of 4-substituted azadienes, triethylamine (2 eq.). After stirring at room temperature for 1 min, the solution was evaporated.

In the reactions using triethylamine, the residue was washed with water (3×25 ml). In the other reactions, the residue was washed with ethyl ether (2×15 ml), affording the desired 1,5-diazaanthraquinones.

3,7-Diethyl-1,5-diazaanthraquinone ((4a), $R^3$=Et, $R^4$=$R^2$=H)
Yield, 68%. Mp; 218–220° C.
IR (KBr): 1682.6 (C=O) cm$^{-1}$.
$^1$H-NMR (300 MHz, CDCl$_3$) δ: 8.93 (d, 2H, J=2.1 Hz, H-2,6); 8.50 (d, 2H, J=2.1 Hz, H-4,8), 2,85 (q, 2H, J=7.5 Hz, C$\underline{H}_2$—CH$_3$); 1.35 (t, 3H, J=7.5 Hz, CH$_2$—C$\underline{H}_3$) ppm.
$^{13}$C-NMR (75 MHz,CDCl$_3$) δ: 181.65; 155:68; 146.50; 145,57; 135.54; 130.58; 26.56; 14.83 ppm.
Analysis calculated for C$_{16}$H$_{14}$N$_2$O$_2$: C, 72.1.8; H. 5.26; N, 10.53. Found: C, 71.86; H, 5.50; N, 10.31.

3,7-Dimethyl-1,5-diazaanthraquinone ((4b), $R^3$=Me, $R^4$=$R^2$=H)
(4b) was purified by chromatography on aluminium oxide 90 (standardised, activity II-III), eluting with hexane-ethyl acetate-chloroform (4/1/5). Yield, 40%). Mp>300 C.
IR(KBr): 1680.1 (C=O) cm$^{-1}$.
$^1$H-NMR(300 MHz, CDCl$_3$) δ: 8.95 (d, 2H, J=1.9 Hz, H-2,6); 8.51 (d, 2H, J=1.9 H-4,8); 2.58 (s, 6H, 2 CH$_3$) ppm.
$^{13}$C-NMR (75 MHz CDCl$_3$) δ: 181.42; 156.07; 146.15; 139.55; 135.54; 130.22; 18.95 ppm.
Analysis calculated for C$_{14}$H$_{10}$N$_2$O$_2$: C, 70.58; H, 4.20; N, 11.76. Found: C, 69.70; H, 4.59; N, 11.54.

4,8-Dimethyl-1,5-diazaanthraquinone ((4c), $R^2$=$R^3$=H, $R^4$=Me)
Yield, 88%. Mp, 253–254° C.
IR (KBr): 1682,5 (C=O) cm$^{-1}$.
$^1$H-NMR (300 MHz, CDCl$_3$) δ: 8.85 (d, 2H, J=5.1 Hz, H-2,6); 7.3 (dd, 2H, J=5.0 Hz, H-3,7); 2.53 (s, 6H, 2 CH$_3$) ppm.
$^{13}$C-NMR (75 MHz, CDCl$_3$) δ: 185.03; 154.23; 150.10; 145.71; 134.21; 128.17; 21.08 ppm.
Analysis calculated for C$_{14}$H$_{10}$N$_2$O$_2$: C, 70.58; H, 4.20; N, 11.76. Found: C, 69.16; H, 4.49, N, 11.43.

4,8-Diethyl-3,7-dimethyl-1,5-diazaanthraquinone ((4d), $R^2$=H, $R^3$=Me, $R^4$=Et)
Yield, 70%. Mp, 180–182° C.
IR (KBr): 1680.0 (C=O) cm$^{-1}$.
$^1$H-NMR (300 MHz, CDCl$_3$) δ: 8.81 (s, 2H, H-2,6); 3.19 (q, 4H, J=7.9 Hz, C$\underline{H}_2$—CH$_3$); 2.53 (s, 6H, 2 CH$_3$); 1.31 (t, 6H, J=7.9 Hz, CH$_2$—C$\underline{H}_3$) ppm.
$^{13}$C-NMR (75 MHz, CDCl$_3$) δ: 181.3; 156.01; 152.78; 141.9; 137.60; 129.30; 23.08; 16.30; 14.21 ppm.
Analysis calculated for C$_{18}$H$_{18}$N$_2$O$_2$: 73.47; H, 6.12; N, 9.52. Found: C, 73.08; H, 6.49; N, 9.17.

Unsymmetrically Substituted 1,5-Diazaanthraquinones
6Bromo4-chloroquinoline-5,8-dione (10)

To a cooled (0° C.) solution of 6-bromo-4-chloro-5,8-dimethoxyquinoline (compound 9) (215 mg, 0.71 mmol) in acetonitrile (10 ml) was added a cooled solution of cerium ammonium nitrate (2 g, 3.67 mmol) in water (10 ml), with stirring. The solution was stirred at room temperature for 90 min, diluted with water (20 ml) and extracted with chloroform (3×60 ml). The chloroform layers were joined, dried over sodium sulphate and evaporated, yielding 153 mg (79%) of compound 10.

$^1$H-NMR(250 MHz, CDCl$_3$) δ: 8,75 (d, 1H J=5,1 Hz, H-2); 7,61 (d, 1H, J=5,1 Hz, H-3); 7,53 (s, 1H, H-7) ppm.
$^{13}$C-NMR(63 MHz, CDCl$_3$) δ: 179.37 and 175.60 (C-5 and C-8); 153,83 (C-2), 149,05 (C-8a); 145,88 (C-6); 140,99 (C-4); 138,93 (C-7); 130,71 (C-3); 125,05 (C-4a) ppm.

8-Chloro-3-methyl-1,5-diazaanthraquinone (11a)

To a solution of quinone 10 (318 mg, 1.17 mmol) in acetonitrile (10 ml) was added a solution of methacrolein dimethylhydrazone (224 mg, 2 mmol) in ethyl ether (2 ml). The violet solution was stirred at room temperature for 16 h and evaporated to dryness. The residue was chromatographed on silica gel, eluting with ethyl acetate-dichloromethane (4:1), to yield, 241 mg (80%) of compound (11a) and 11 mg (4%) of its 1,8-diaza regioisomer. Data for compound (11a):

Mp, 208–210° C. IR (KBr) ν: 1691 (C=O) cm$^{-1}$
$^1$H-NMR(250 MHz, CDCl$_3$) δ: 8.93 (d, 1H, J=2 Hz, H-2); 8.90 (d, 1H, J=5.1 Hz, H-6); 8.43 (d, 1H, J=2 Hz, H-4); 7,75 (d, 1H J=5.1 Hz, H-7); 2,55 (s, 3H, CH$_3$) ppm.
$^{13}$C-NMR (63 MHz, CDCl$_3$) δ: 180.82; 179.61; 156.97; 154.04; 150.41; 146,55; 135.36; 131.49; 130.01; 128.91; 127.85; 19.06 ppm.

Analysis calculated for $C_{13}H_7N_2O_2Cl$: 60.38; H, 2.71; N, 10.83. Found: C, 60.20; H, 2.58; N, 10.99.

8-Chloro-1-dimethylamino-4-methyl-1,4-dihydro-1,5-diazaanthraquinone (12a)

To a solution of quinone 10 (77 mg, 0.29 mmol) in acetonitrile (5 ml) was added a solution of crotonaldehyde dimethylhydrazone (52 mg, 0.46 mmol) in ethyl ether (1 ml). The violet solution was stirred at room temperature for 22 h. The solvent and excess azadiene were evaporated under reduced pressure, and the residue was chromatographed on silica gel, eluting with ethyl acetate. Yield, 76 mg (89%) of compound (12a). Mp, ° C.

R(KBr) ν: 1667, 1640 (C=O) cm$^{-1}$.
$^1$H-NMR (250 MHz, CDCl$_3$) δ: 8.73 (d, 1H, J=5.3 Hz, H-6); 7.53 (d, 1H, J=5.3 Hz, H-7); 6.25 (d, 1H, J=7.9 Hz, H-2); 5.20 (dd, 1H, J=7.9 and 5.1 Hz, H-3); 3,76 (m, 1H, H-4); 2,69 (s, 6H, N(CH$_3$)$_2$); 1.17 (d, 3H, J=6.6 Hz, CH$_3$) ppm.
$^{13}$C-NMR (63 MHz, CDCl$_3$) δ: 180.20; 177.92; 152.74; 152.39; 149.48; 146.37; 143.09; 128.75; 121.46; 120.30; 120.16; 113.34; 44.85; 26.04; 23.95 ppm.

Analysis calculated for $C_{15}H_{14}ClN_3O_2$: 59.34; H, 4.61; N, 13.83. Found: C, 59.81; H, 4.23; N, 14.02.

4-Chloro-8-methyl-1,5-diazaanthraquinone (13a)

A sample of compound (12a) (43 mg, 0.14 mmol) was heated at 110° C. and 0.1 torr during 2 h and washed with ethyl ether (2×5 ml) and chloroform (2×5 ml). The residue (22 mg, 60%) was identified as compound (13a). Mp>300° C.

IR (KBr) ν: 1689 (C=O) cm$^{-1}$.
$^1$H-NMR 250 MHz, DMSO) δ: 8.92 (d, 1H, J=5.1 Hz, H-6); 8.87 (d, 1H, J=4.8 Hz, H-2); 7.97 (d, 1H, J=5.1 Hz, H-7); 7,70 (d, 1H, J=4.8 Hz, H-3); 2,77 (s, 3H, CH$_3$)ppm.

Analysis calculated for $C_{13}H_7ClN_2O_2$: 60.38; H, 2.71; N, 10.83. Found: C, 60.79; H, 2.23; N, 11.11.

4-Chloro-8-(o-nitrophenyl)-1,5-diazaanthraquinone (13b)

(13b) was prepared as it was previously described (see United Kingdom Patent Application No. 9708751.4, see PCT/GB 98/01239).

4-Dimethylamino-8-methyl-1,5-diazaanthraquinone (14a)

A solution of compound (12a) (21 mg, 0.11 mmol) in THF (2 ml) and 6N aqueous HCl (2 ml) was heated at 80° C. for 1 h. The reaction mixture was saturated with solid sodium carbonate and extracted with chloroform (3×5 ml) and ethyl acetate (3×5 ml). The combined organic layers were dried over sodium sulphate and evaporated, yielding 16 mg (88%) of compound (14a). Mp, 97–100° C.

IR (KBr) ν: 1683 and 1654 (C=O) cm$^{-1}$;
$^1$H-NMR (250 MHz, CDCl$_3$) δ: 8.84 (d, 1H, J=4.9 Hz, H-6); 8.53 (d, 1H, J=5.1 Hz, H-2); 7.44 (d, 1H, J=4.9 Hz, H-7); 6.99 (d, 1H, J=6.1 Hz, H-3); 3.11 (s, 6H, N(CH$_3$)$_2$); 2.86 (s, 3H, CH$_3$) ppm.

Analysis calculated for $C_{15}H_{12}N_3O_2Cl$: 67.44; H, 4.68; N, 15.72. Found: C, 67.91; H, 3.08; N, 15.43.

Antitumour Activity

Cells were maintained in logarithmic phase of growth in Eagle's Minimum Essential Medium, with Earle's Balanced Salts, with 2.0 mM L-glutamine, with non-essential amino acids, without sodium bicarbonate (EMEM/neaa); supplemented with 10% Fetal Calf Serum (FCS), 10$^{-2}$ M sodium bicarbonate and 0,1 g/l penicillin-G+streptomycin sulfate.

A screening procedure has been carried out to determine and compare the antitumour activity of these compounds, using an adapted form of the method described by Raymond J. Bergeron, Paul F. Cavanaugh Jr., Steven J. Kline, Robert G. Hughes, Jr., Gary T. Elliot and Carl W. Porter. Antineoplastic and antiherpetic activity of spermidine catecholamide iron chelators. *Biochem. Bioph. Res. Comm.* 1984, 121, 848–854. The antitumour cells employed were P388 (ATCC CCL-46) (suspension culture of a lymphoid neoplasm from DBA/2 mouse), A549 (ATCC CCL-185) (monolayer culture of a human lung carcinoma), HT-29 (ATCC HTB-38) (monolayer culture of a human colon carcinoma) and SK-MEL-28 (ATCC HTB-72) (monolayer culture of a human melanoma).

P388 (ATCC CCL-46) cells were seeded into 16 mm wells at 1×10$^4$ cells per well in 1 ml aliquots of MEM 5FCS containing the indicated concentration of drug. A separate set of cultures without drug was seeded as control growth to ensure that cells remained in exponential phase of growth. All determinations were carried out in duplicate. After three days of incubation at 37° C., 10% CO$_2$ in a 98% humid atmosphere, an approximately IC$_{50}$ was determined by comparing the growth in wells with drug to the growth in wells control.

A549 (ATCC CCL-185), HT-29 (ATCC HTB-38) and SK-MEL-28 (ATCC HTB-72) cells were seeded into 16 mm wells at 2×10$^4$ cells per well in 1 ml aliquots of MEM 10FCS containing the indicated concentration of drug. A separate set of cultures without drug was seeded as control growth to ensure that cells remained in exponential phase of growth. All determinations were carried out in duplicate. After three days of incubation at 37° C., 10% CO$_2$ in a 98% humid atmosphere, the wells were stained with 0.1% Crystal Violet. An approximately IC$_{50}$ was determined by comparing the growth in wells with drug to the growth in wells control.

The results of the in vitro cytotoxic assays for these compounds (4a), (4b), (4c), (4d), (11a), (12a), (13a), (13b), and (14a) with the cellular lines P388 (ATCC CCL-46), A549 (ATCC CCL-185), HT-29 (ATCC HTB-38) and SK-MEL-28 (ATCC HTB-72) are shown in the following Table.

TABLE

| Compound | IC$_{50}$ (µM) | | | |
| --- | --- | --- | --- | --- |
| | P388 | A549 | HT-29 | SK-MEL-28 |
| (4a) | 0.45 | 0.05 | 0.19 | 0.05 |
| (4b) | 7.35 | 0.05 | 0.51 | 0.11 |
| (4c) | 4.20 | 0.50 | 1.05 | 1.05 |
| (4d) | 3.40 | 3.40 | 3.40 | 3.40 |
| (11a) | 0.15 | 0.03 | 0.04 | 0.03 |
| (12a) | 3.29 | 0.33 | 1.65 | 0.33 |
| (13a) | 3.87 | 0.19 | 1.93 | 0.19 |
| (13b) | 0.27 | 0.03 | 0.27 | 0.07 |
| (14a) | 9.36 | 0.37 | 0.94 | 0.37 |

What is claimed is:

1. A compound having the formula (I):

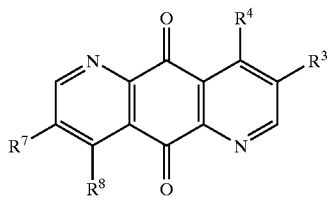

wherein $R^3$, $R^4$, $R^7$, and $R^8$ are independently selected from the group consisting of hydrogen, lower alkyl, halogen, amine, mono(lower)alkylamine, phenyl, or substituted phenyl, wherein the phenyl group is substituted with from one to four substituents independently selected from the group consisting of lower alkyl, halogen, amine, mono(lower)alkylamine, di(lower)alkylamine, nitro, hydroxy, lower alkoxy, or trifluoromethyl, with the exception of the compounds in which:

$R^3$, $R^4$, $R^7$, $R^8$ are all hydrogen;

$R^3$ and $R^7$ are hydrogen, $R^4$ is chlorine, and $R^8$ is a 2-nitrophenyl group;

$R^3$ and $R^7$ are hydrogen, $R^4$ is amino, and $R^8$ is a 2-nitrophenyl group, $R^3$, $R^7$ and $R^8$ are hydrogen and $R^4$ is chlorine, and $R^4$, $R^7$ and $R^8$ are hydrogen and $R^3$ is methyl.

2. A compound according to claim 1, which is selected from a compound of formula (4),

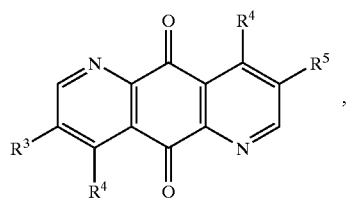

formula (8)

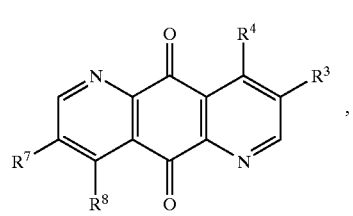

formula (11)

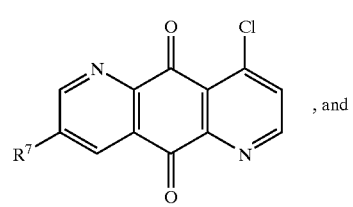

formula (13)

, and

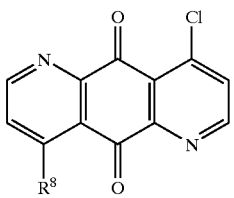

formula (14)

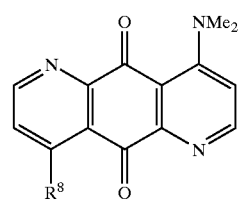

wherein $R^3$, $R^4$, $R^7$, and $R^8$ are independently selected from the group consisting of hydrogen, lower alkyl, halogen, amine, mono(lower)alkylamine, phenyl, or substituted phenyl wherein the phenyl group is substituted with from one to two substituents independently selected from the group consisting of lower alkyl, halogen, amine, mono(lower) alkylamine, di(lower)alkylamine, nitro, hydroxy, lower alkoxy, or trifluoromethyl.

3. A compound according to claim 1 or 2, wherein the substituent groups $R^3$, $R^4$, $R^7$, and $R^8$ are chosen from hydrogen, methyl, ethyl, chlorine, dimethylamine, and nitrophenyl.

4. A compound according to claim 1 which is selected from:

3,7-diethyl-1,5-diazaanthraquinone
3,7-dimethyl-1,5-diazaanthraquinone
4,8-dimethyl-1,5-diazaanthraquinone
4,8-diethyl-3,7-dimethyl-1,5-diazaanthraquinone
8-chloro-3-methyl-1,5-diazaanthraquinone
8-chloro-1-dimethylamino-4-methyl-1,4dihydro-1,5-diazaanthraquinone
4-chloro-8-methyl-1,5-diazaanthraquinone and
4-dimethylamino-8-methyl-1,5-diazaanthraquinone.

5. A pharmaceutical composition which comprises a compound of the formula (I):

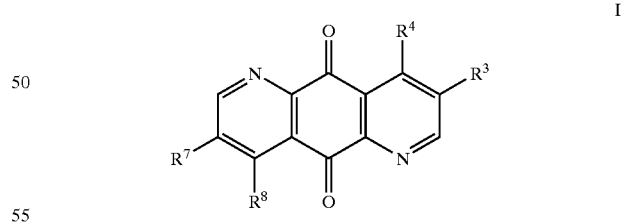

wherein $R^3$, $R^4$, $R^7$, and $R^8$ are independently selected from the group consisting of hydrogen, lower alkyl, halogen, amine, mono(lower)alkylamine, di(lower)alkylamine, phenyl, or substituted phenyl, wherein the phenyl group is substituted with from one to four substituents independently selected from the group consisting of lower alkyl, halogen, amine, mono(lower)alkylamine, di(lower)alkylamine, nitro, hydroxy, lower alkoxy, or trifluoromethyl, together with a pharmaceutical carrier.

6. A composition according to claim 5, wherein the compound is selected from a compound of formula (4),

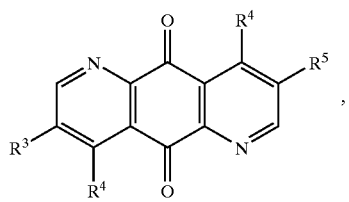

formula (8)

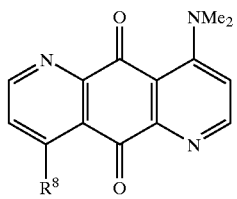

formula (11)

wherein $R^3$, $R^4$, $R^7$, and $R^8$ are independently selected from the group consisting of hydrogen, lower alkyl, halogen, amine, mono(lower)alkylamine, phenyl, or substituted phenyl wherein the phenyl group is substituted with from one to two substituents independently selected from the group consisting of lower alkyl, halogen, amine, mono(lower)alkylamine, di(lower)alkylamine, nitro, hydroxy, lower alkoxy, or trifluoromethyl.

7. A composition according to claim 5 or 6, wherein the substituent groups $R^3$, $R^4$, $R^7$, and $R^8$ are chosen from hydrogen, methyl, ethyl, chlorine, dimethylamine, and nitrophenyl.

formula (13)

8. A composition according to claim 5, wherein the compound is selected from:
3,7-diethyl-1,5-diazaanthraquinone
3,7-dimethyl-1,5-diazaanthraquinone
4,8-dimethyl-1,5-diazaanthraquinone
4,8-diethyl-3,7-dimethyl-1,5-diazaanthraquinone
8-chloro-3-methyl-1,5-diazaanthraquinone
8-chloro-1-dimethylamino-4-methyl-1,4-dihydro-1,5-diazaanthraquinone
4-chloro-8-methyl-1,5-diazaanthraquinone
4-chloro-8-(o-nitrophenyl)-1,5-diazaanthraquinone and
4-dimethylamino-8-methyl-1,5-diazaanthraquinone.

formula (14)

9. A method of treating a mammal affected by a malignant tumor selected from the group consisting of lymphoid neoplasm, lung carcinoma, colon carcinoma or melanoma, which comprises administering to the mammal in need thereof a therapeutically effective amount of a compound according to any one of claims 1, 2 or 4, or a pharmaceutical composition according to any one of claims 5, 6 or 8.

* * * * *